United States Patent [19]

McCormick

[11] 4,267,280
[45] May 12, 1981

[54] CONTROLLED RELEASE PESTICIDES AND METHOD OF PREPARATION

[76] Inventor: Charles L. McCormick, 2308 Clayton Pl., Hattiesburg, Miss. 39401

[21] Appl. No.: 59,169

[22] Filed: Jul. 20, 1979

Related U.S. Application Data

[63] Continuation-in-part of Ser. No. 766,522, Feb. 7, 1977, abandoned, and a continuation-in-part of Ser. No. 929,749, Jul. 31, 1978, abandoned.

[51] Int. Cl.³ ..................... C08G 18/04; C08G 18/64
[52] U.S. Cl. ........................................ 525/56; 71/93; 71/117; 71/DIG. 1; 424/19; 424/78; 424/81; 424/93; 424/358; 521/137; 525/123; 525/128; 525/131; 528/75; 536/2; 536/31; 536/45; 536/55
[58] Field of Search ................. 525/123, 131, 128, 56; 536/61, 85; 424/78, 81, DIG. 8; 528/73

[56] References Cited

U.S. PATENT DOCUMENTS

| | | | |
|---|---|---|---|
| 3,269,900 | 8/1966 | Rubin | 424/32 |
| 3,966,902 | 6/1976 | Chromocek | 424/DIG. 8 |
| 4,177,038 | 12/1979 | Biebricher et al. | 525/123 |

FOREIGN PATENT DOCUMENTS 855181 11/1970 Canada.
863310 2/1971 Canada.

OTHER PUBLICATIONS

Scher (Editor), Controlled Release Pesticides, ACS Symposium Series 53, (1977), pp. 112–125.

*Primary Examiner*—H. S. Cockeram
*Attorney, Agent, or Firm*—Quarles & Brady

[57] ABSTRACT

Pesticide polymers comprising a polymer with a macromolecular backbone and pendant groups having pesticidal groups chemically linked thereto are prepared by reacting a pesticide having a replaceable hydrogen with a multifunctional isocyanate to form a pesticide-isocyanate adduct and then reacting the adduct with the polymer substrate in a mutual solvent to form the pesticide polymers. The chemical linkages connecting the pesticide-adduct to the pendant groups are cleaved under environmental conditions of use to controllably release an effective amount of the active pesticide.

10 Claims, No Drawings

CONTROLLED RELEASE PESTICIDES AND METHOD OF PREPARATION

RELATED APPLICATION

This is a continuation-in-part application of my earlier applications Ser. No. 766,522 filed Feb. 7, 1977, and Ser. No. 929,749 filed July 31, 1978, both now abandoned.

BACKGROUND OF THE INVENTION

The present invention relates to controlled release pesticides and to a method of preparing such pesticides.

In the past there have been numerous efforts made to develop controlled release or sustained release pesticides. One approach has been to entrap the pesticide in a protective polymeric coating such as, for example, the method described in U.S. Pat. No. 3,269,900. Another approach has been to chemically couple the pesticide directly to a natural organic polymeric substrate such as lignin as described in Canadian Pat. No. 863,310 and still another approach has been to use a bridging compound to connect the pesticide to the natural polymeric substrate such as that described in Canadian Pat. No. 855,181. In addition, pesticides have been dissolved in waxes, incorporated in emulsions and combined with large amounts of inert carriers all in an effort to obtain sustained released pesticide compositions.

None of the above described approaches is completely without disadvantages. For example, entrapping the pesticide in a polymer is relatively expensive; the use of a natural substrate may result in a product which is not only of nonuniform consistency from batch to batch but which is also bulky to transport and handle and the incorporation of pesticides in emulsions, waxes, and compositions including inert carriers may result in nonrelease or uneven release of the active ingredient.

SUMMARY OF THE INVENTION

It is the general object of the present invention to disclose a novel method of preparing novel, biodegradable, polymer systems containing known pesticides which polymer systems will hydrolyze or depolymerize to yield the pesticides.

It is a further object to disclose novel, biodegradable, polymer systems that are hydrolyzed or depolymerized over a reasonable period of time to release pesticide materials at a controlled rate.

In the preferred method of the present invention, a pesticide having an active hydrogen is reacted with a di, tri or multifunctional isocyanate coupling agent to form a pesticide-isocyanate adduct which is then reacted with a polymeric polyol such as polyvinyl alcohol in a mutual solvent, such as dimethylacetamide, to obtain a novel, biodegradable polymer system which under conditions of use releases the pesticide at a controlled and sustained rate.

These and still other objects of the invention will be apparent to those skilled in the art from the disclosure which follows.

DESCRIPTION OF THE PREFERRED EMBODIMENT

The novel polymer system of the present invention may be represented by the following formula:

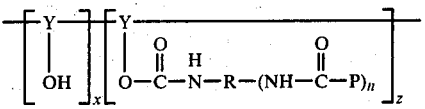

in which

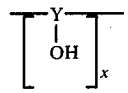

is the unreacted portion of a polymeric polyol of the formula

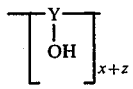

in which $x+z$ is from 10 to $1.0 \times 10^7$, x is less than $x+z$ and can be zero, R is the aliphatic or aromatic portion of an isocyanate of the formula $OCN-R-(NCO)_n$ in which n is 1 to 10, and P is the pesticidal remainder of a pesticide of the formula P—H from which H, an active hydrogen, has been removed. The extent of reaction of the hydroxy functions in

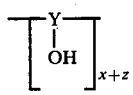

may be from about 1% to 100%.

When an amount of di, tri or multifunctional isocyanates in excess of the amounts needed to generate the pesticide-isocyanate adduct are utilized, the isocyanates react with additional hydroxyl functions in formula I to form cross-linked or network polymers.

The novel polymer systems may be prepared by reacting a pesticide having an active hydrogen with a di, tri or multifunctional isocyanate to form a pesticide-isocyanate adduct, which is then reacted with the polymer in a mutual solvent to form the desired polymeric system.

The process may be represented as follows:

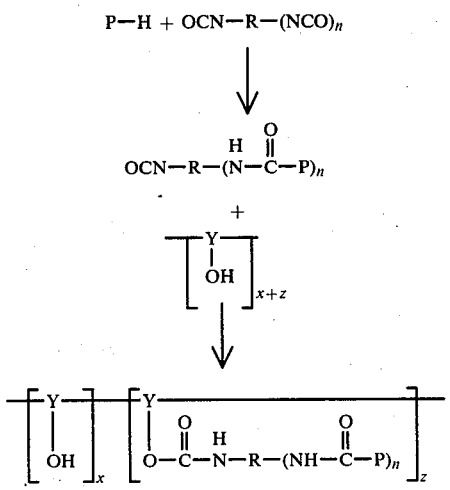

in which all symbols are as previously defined.

The term pesticide as employed herein is any active material used for biologic control of unwanted organisms including in particular insecticides, fungicides, herbicides, nematocides and other biocides, and includes plant growth regulators and the like materials utilizable in a field environment.

The pesticides that may be used with the present invention are those pesticides which have an active hydrogen or which can be modified to have an active hydrogen which can be used as a means of achieving reaction with the isocyanate to form a hydrolyzable bond. The active hydrogen atom may be coupled directly to an oxygen, nitrogen, or sulfur atom which may be within a substituent group consisting of hydroxyl, sulfyhydryl, amino, imino, carboxyl, amido, imido, sulfonamido, sulfonimido, phosphoramido, phosphorimido, thiophosphoramido, or thiophosphorimido.

Representative of the pesticides which may be employed as starting materials in the process are the following:

propen-1-ol-3
2-(ethylamine)-4-(isopropylamino)-6-(methylthio-s-triazine)
3-amino-5-triazole
Ammonium Sulfamate
Arsenic Acid
methyl sulfanilyl carbamate
2-chloro-4-(ethylamino)-6-(isopropylamino)-s-triazine
(4-chloro-2-butynyl N-3(-chlorophenyl) carbamate
4-chloro-2-oxobenzothiazolin-3-ylacetic acid
N-butyl-N-ethyl-$\alpha,\alpha,\alpha$-trifluoro-2,6-dinitro-p-toluidine
[S-(O,O-diisopropyl phosphorodithioate) ester of N-(2-mercaptoethyl) benzene sulfonamide]
3-isopropyl-1H-2,1,3-benzothiadiazin-4-(3H)-one 2,2-dioxide
(benzamidooxy) Acetic Acid
Methyl 5-(2,4-dichlorophenoxy)-2-Nitrobenzoate
5-bromo-3-sec-butyl-6-methyluracil
3,5-dibromo-4-hydroxybenzonitrile
hydroxydimethylarsine oxide
D-N-ethyllactamide carbanilate (ester)
3-Amino-2,5-dichlorobenzoic Acid
3-(4-bromo-3-chlorophenyl)-1-methoxy-1-methylurea
methyl-2-chloro-9-hydroxyfluorene-9-carboxylate
3-[p-(p-chlorophenoxy)phenyl]-1,1-dimethylurea
isopropyl-m-chlorocarbanilate
2[[4-chloro-6-(ethylamino)-s-triazin-2-yl]Amino]-2-methylpropionitrile
2-chloro-4-(cyclopropylamino)-6-(isopropylamino)-s-triazine
(2,4-dichlorophenoxy)acetic acid
2,2-dichloropropionic Acid
4-(2,4-dichlorophenoxy)butyric acid
Ethyl m-hydroxycarbanilate carbanilate
3,6-dichloro-o-anisic acid
2-(2,4-dichlorophenoxy)propionic acid
$N^4,N^4$-diethyl-$\alpha,\alpha,\alpha$-trifluoro-3,5-dinitrotoluene-2,4-diamine
2-sec-butyl-4,6-dinitrophenol
2,4-bis(isopropylamino)-6-(ethylthio)-s-triazine
3-(3,4-dichlorophenyl)-1,1-dimethylurea
7-oxabicyclo [2,2,1]heptane-2,3-dicarboxylic acid
2-chloroethylphosphonic acid
(2,3,6-trichlorophenyl)acetic acid
1,1-dimethyl-3-phenylurea mono(trichloroacetate)
1,1-dimethyl-3-($\alpha,\alpha,\alpha$-trifluoro-m-tolyl)urea
n-butyl-9-hydroxyfluorene-(9)-carboxylate N-(phosphonomethyl) glycine
N,N-bis(phosphonomethyl) glycine
2-methoxy-4-ethylamino-6-sec-butylamino-s-triazine
4-hydroxy-3,5-diiodobenzonitrile
3-(m-hydroxyphenyl)-1,1-dimethylurea
3-(3,4-dichlorophenyl)-1-methoxy-1-methylurea
methanearsonic acid
N-[3-[(1,1,1-trifluoromethylsulfonyl)Amino]-4-methylphenyl]acetamide
1,1,1-trifluoro-N-[2-methyl-4-(phenylsulfonyl)phenyl]-methanesulfonamide
2-methyl-4-chlorophenoxyacetic acid
4-[(4-chloro-o-tolyl)oxy]butyric acid
2-[(4-chloro-o-tolyl)oxy]propionic acid
4-amino-6-tert-butyl-3-(methylthio)-as-triazin-5(4H) one
1,2-dihydro 3,6-pyridazinedione
3-(p-chlorophenyl)-1,1-dimethylurea
1-naphthalene acetic acid
N-1-naphthylphthalamic acid
6-tert-butyl-3-isopropylisoxazolo-[5,4-d]pyrimidin-4(5H)-one
3-(hexahydro-4,7-methanoindan-5-yl)-1,1-dimethylurea
4-chloro-5-(methylamino)-2-($\alpha,\alpha,\alpha$-trifluoro-m-tolyl)-3-(21t)-pyridazinone
3,5-dinitro $N^4,N^4$-dipropylsulfanilamide
methyl m-hydroxycarbanilate m-methylcarbanilate
4-amino-3,5-6-trichloropicolinic acid
p-chlorophenyl N-methylcarbamate
2,4-bis(isopropylamino)-6-methoxy-s-triazine
2,4-bis(isopropylamino)-6-(methylthio)-s-triazine
N,-(1,1-dimethylpropynyl)-3,5-dichlorobenzamide
3',4'-dichloropropionanilide
2-chloro-4,6-bis(isopropylamino)-s-triazine
isopropyl carbanilate
5-amino-4-chloro-2-phenyl-3(2H)-pyridazinone
1-(2-methylcyclohexyl)3-phenylurea
2-(2,4,5-trichlorophenoxy)propionic acid
2-chloro-4,6bis(ethylamino)-s-triazine
(2,4,5-trichlorophenoxy)acetic acid
2,3,6-trichlorobenzoic acid
trichloracetic acid
3-tert-butyl-5-chloro-6-methyluracil
2-chloro-4-ethylamino-6-tert-butylamino-s-triazine
2,6-di-tert-butyl-p-tolyl methylcarbamate
2-methylthio-4-ethylamino-6-tert-butylamino-s-triazine
2,3,5-triiodobenzoic acid
—S-(2,3,3-trichloroallyl)diisopropylthiocarbamate
—S-propyl dipropylthiocarbamate
acroeline phenylhydrazone
2-amino-3-chloro-1,4-naphthoquinone
4-amino pteroylglutamic acid
p-tert-amyl phenol
2-(3'-pyridyl) piperidine
2,4-dichloro-6-(2-chloroanil-o)-1,3,5 triazine
1-decanol
1-(1-naphthyl)-2-thiourea
2-iodobenzanilide
1,4-benzoquinone-1-benzoyl-hydrozone-4-oxime
4-chloro-3,5-xylenol
n-butyl-p-hydroxybenzoate
benzoyl-8-hydroxyquinoline salicylate
3-(sec-butyl) phenyl-N-methylcarbamate
3,5-dibromo-4-hydroxybenzaldehyde O-(2,4-dinitrophenyl) oxime
2-bromo-4'-hydroxyacetophenone
isopropyl 4,4'-dibromobenzilate
3,5-dibromo-4-hydroxybenzonitrile 2-ethyl-2-butyl-1,3-propanediol
1-naphthyl methylcarbamate
2,3-dihydro-2,2-dimethyl-benzofuran-7yl-methylcarbamate
Chlorobenzenesulfonamide
monochloroacetic acid
cis-3-chloroacrylic acid
3-amino-2,5-dichlorobenzoic acid
2,2'thiobis(4-chloro-6-methylphenol)
3-(4-bromo-3-chlorophenyl)-1-methoxy-1-methylurea
1-methyl-2-propynyl-m-chlorocarbanilate
ethyl 4,4'-dichlorobenzilate
4-chloro-m-cresol
4-chloro-2-cyclopentyl phenol
5-chloro-4-methyl-2-propionamidothiazole
2,2,3-trichloropropionic acid
isopropyl 4,4'-dichlorobenzilate
6-chloro thymol
3,5-dichloro-4-hydroxybenzonitrile
O-benzyl-p-chlorophenol
3-(α-acetonyl-4-chlorobenzyl)-4-hydroxycoumarin
2-(3-chlorophenoxy)α-propionamide
2-(3-chlorophenoxy) propionic acid
2-chlorophenyl-N-methylcarbamate
2-(4-chlorophenoxy) propionic acid
O-cresol
m-cresol
p-cresol
α-cyano-B-(2,4-dichloro)-cinnamic acid
N-cyclohexyl 2,5-dimethyl-3-furamide
3-(4-cyclopropylphenyl)-1,1-dimethylurea
3-cyclo-octyl-1,1-dimethylurea
O,O-dimethyl O-p-sulfamoylphenyl phosphorothioate
2,2-dichloropropionic acid
1,3-bis (1-hydroxy-2,2,2-trichloroethyl)urea
3,6-dichloro-2-methoxybenzoic acid
2,2-methylenebis (4-chlorophenol)
2,4-dichloro phenoxy acetamide
2(3,4-dichlorophenoxy)propionic acid
1,1-bis(p-chlorophenyl)-2,2,2-trichlorethanol
O,O-dimethyl S-(N-methyl-carbamoylmethyl) phosphorodithioate
4,6-dinitro-o-cresol
2,4-dinitro-6-cyclohexyl phenol
2,4-dinitrophenol
2,5-dichloro-3-nitrobenzoic acid
2,4-dinitro-6-sec-butylphenol
2,4-dinitro-6-tert-butylphenol
1,1-bis(p-chlorophenyl)ethyl carbinol
fluoroacetamide
fluoroacetanilide
3-hydroxy-5-methylisoxazole
2-hydroxymethyl-4-chlorophenyloxyacetic acid
3-inddylpropionic acid
4-chloro-2-methylphenoxy acetic acid
4-(4-chloro-2-methylphenoxy)butyric acid
3-methyl-2,4-dinitro-6-tertbutyl phenol
bishydroxy coumarin
methyl p-hydroxybenzoate
cyclopentane carboxylic acid
B-naphthol
α,α-bis (p-chlorophenyl)-3-pyridine-methanol
nonylic acid
2,3,4,5,6-pentachlorobenzylalcohol
pentachlorophenol
2-phenylcyclohexanol
2-hydroxy diphenyl
N-phenyl-N'-3-thiolane-1-dioxide hydrazide
4-amino-3,5,6-trichloropicdinic acid
2-hydroxybenzhydroxamic acid
2,4hexadienoic acid
1,1'methylenedi-2-naphthol
2,3,6-trichlorobenzoic acid
3,4',5-tribromosahcylanilide
3-trifluoromethyl-4nitrophenol
2,3,5-triiodobenzoic acid
3,5,6-trichloro-2-methoxybenzoic acid
2,4,6-trichlorophenol
2,4,5-trichlorophenol
2-(hydroxymethyl)-2-nitrol-1,3-propanediol
2,3,6-trichlorobenzyloxypropanol
10-undecenoic acid
2,4-dimethyl phenol Obviously the foregoing list is not complete for as previously indicated any pesticide having an active hydrogen, or which can be modified to have an active hydrogen may be employed.

The pesticides which are especially preferred are: 2,4-dichlorophenoxy acetic acid (2,4-D), 2,4,5-trichlorophenoxy acetic acid, 2,2-dichloropropionic acid, 4-(2,4-dichlorophenoxy-butyric acid, and the relatively new pesticide 4-amino-6-tert-butyl-3-(methylthio)-as-triazine-5(4H)one which is available under the name metribuzin.

The multifunctional isocyanates that can be used in the invention may be represented by the formula:

$$OCN-R-(NCO)_n$$

in which n is 1 to 10 and preferably1 to 3, and R is a linking aliphatic or aromatic group. Typical types of isocyanates which may be employed are aliphatic polyisocyanates, cycloaliphatic diisocyanates, aromatic diisocyanates, dicycloaliphatic diisocyanates, and diaryl diisocyanates.

Representative of specific isocyanates that can be employed are the following:
4,4-diphenyl-methane diisocyanate
1,6-hexamethylene diisocyanate
1,5-Naphthalene diisocyanate
Dimers α Trimers of above
p-phenylene diisocyanate
m-phenylene diisocyanate
1-chloro-2,4-phenylene diisocyanate
3,3'-dimethyl-4,4'bisphenylene diisocyanate
3,3'-dimethoxy-4,4'-bisphenylene diisocyanate
4,4'-Bis(2-methyl isocyanotophenyl) methane
4,4'-Bis(2-methoxyisocyanoto phenyl) methane
4,4'-dicyclohexylmethane diisocyanate
2,2,4-trimethylhexamethylene diisocyanate
3,isocyanatomethyl-3,5,5 trimethyl cyclohexylisocyanate, and
The tri isocyanate generated by the reaction of the mole of water with 3 moles of 1,6-hexamethylene diisocyanate.

The polyols intended for use in the invention are polymeric polyols which may be represented by the formula:

in which

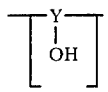

is an organic monomer and x+z may be from 10 to $1.0 \times 10^7$. The polymeric polyols have discernible structures and molecular weights making it possible to prepare polymeric systems that are tailored to contain a definite amount of releasable active pesticide per unit of weight measure.

The polyol which has been found to be especially useful is polyvinyl alcohol which is biodegradable and readily available commercially at reasonable cost. Polyvinyl alcohol is a polymer prepared from polyvinyl acetates by the replacememt of the acetate with hydroxyl groups. Polyvinyl alcohol may be represented by the following formula:

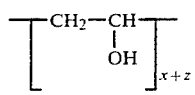

in which x+z is $1 \times 10^2$ to $1 \times 10^7$.

Commercially available polyvinyl alcohols have different contents of residual acetyl groups, different molecular weights, and, therefore, different viscosity characteristics. Generally, the first code number following the trade name indicates the degree of hydrolysis while the second set of numbers indicates the approximate viscosity and centipoise (4% aqueous solution at 20°. Among the polyvinyl alcohols that may be used in the method of the present invention are the low and high molecular weight polymers available as 100% solids from the Aldrich Chemical Company of Milwaukee, Wisconsin.

Other polymers that are candidates for use include:
Polyvinyl Alcohol-polyvinyl acetate copolymers
Polyacrylic Acid
Polymethacrylic Acid
Polyvinyl Amine
Celluslose α and derivates thereof such as:
(1) hydroxy methyl cellulose,
(2) hydroxy ethyl cellulose,
(3) hydroxy propyl cellulose,
(4) carboxymethyl cellulose, and
(5) xanthate derivatives of cellulose and
hydroxy-substituted polysaccharides such as chitin, starches, dextrans, xylans, and pectins.

In the preferred practice of the invention, the isocyanate is dissolved in a suitable solvent and the pesticide is separately dissolved in the same solvent. The pesticide solution then is added to the solution of the isocyanate with stirring. The mixture is allowed to react until a pesticide-isocyanate adduct is formed, e.g., 1 to 2 hours at a temperature of 60°–130° C. The polymer which has been dissolved in the same solvent is then added to the adduct. The resulting mixture is allowed to react until the reaction is complete, e.g., 1 to 4 hours at 80°–120° C. The resulting reaction mixture is then cooled and the polymer system isolated by conventional techniques.

Although dimethylacetamide (DMAC) is a preferred solvent other suitable solvents can be employed such as N,N-dimethyl formamide and dimethyl sulfoxide. A useful solvent for polysaccharide polymers is a solvent mixture of N,N-dimethyl acetamide or N,N-dimethyl formamide and 5% lithium chloride or lithium nitrate.

The following examples are presented to illustrate the practice of the invention.

EXAMPLE 1

Linear Polymer System 12.18 g (0.0487 moles) of p,p′diphenylmethane diisocyanate (MDI) was dissolved in dimethylacetamide (DMAC) and placed in a 3-necked round-bottomed flask equipped with stirrer, condenser, thermometer, and addition funnel. 10.43 g (0.0487 moles) of 4-amino-3-methylthio-5-5-butyl-1,2,4-triazine-5-one metribuzin in 100 ml of DMAC was added to the stirring solution and allowed to react for one hour at 110° C. 10.0 g of polyvinyl alcohol (99% hydrolyzed, high molecular weight) was dissolved in 200 ml of hot DMAC. The solution was then added to the metribuzin - MDI adduct. The resulting solution was allowed to react at 100° C. for two hours. The resulting solution gelled on cooling. The product was precipitated using methanol. The resulting white solid was filtered and dried in a vacuum oven at low pressures.

EXAMPLE 2

Linear Polymer System

The procedure of Example 1 was carried out under a dry stream of nitrogen using the same conditions. Quantities: MDI (5.2 g, 0.021 moles); metribuzin (4.5 g; 0.021 moles); polyvinyl alcohol (99% hydrolyzed, high molecular weight) (5.0 g). A white solid polymer was obtained.

EXAMPLE 3

Highly Cross-linked Systems

Using the same apparatus as described in Example 1, the following reaction was carried out:

Metribuzin (8.56 g, 0.04 moles) was dissolved in 100 ml of DMAC and added to 20.0 g of MDI in 150 ml DMAC. The solution was heated to 110° C. and allowed to react for two hours. 10.0 g of polyvinyl alcohol (99% hydrolyzed, high molecular weight) was dissolved in 200 ml of DMAC and added in one portion to the reaction solution. After 3–5 minutes of fast agitation, a light-amber colored gel formed. The gel was converted to a white microporous highly cross-linked solid. The polymer was dried overnight under vacuum. EXAMPLE 4

Highly Cross-linked Solid

The procedure of Example 3 was repeated. A controlled release, highly cross-linked polymer was prepared using the following quantities:

20.0 g (0.08 moles) MDI, 8.56 (0.04 moles) metribuzin; 10.0 g of polyvinyl alcohol (99% hydrolyzed, high molecular weight). Precipitation was followed by extensive drying under vacuum at room temperature to obtain the desired polymer system.

EXAMPLE 5

Moderately Cross-linked System

The procedure of Example 4 was repeated using the following: metribuzin 4.5 g; MDI 6.2 g; polyvinyl alcohol (99% hydrolyzed, high molecular weight) 5.0 g. The resulting gel was precipitated in methanol yielding a microporous solid which was dried overnight under vacuum.

EXAMPLE 6

Linear System 2,4-dichlorophenoxy acetic acid (2,4-D) (8.84 g) was dissolved in 100 ml of DMAC and added to a stirring solution of 10.0 g of MDI in a 500 ml round-bottomed, 3-necked flask equipped with condenser, thermometer, addition funnel and stirrer. The reaction was allowed to proceed at 80° C. 10.0 g of polyvinyl alcohol (99% hydrolyzed, high molecular weight) dissolved by stirring in hot DMAC, was added to the reaction solution and stirred at 110° C. for two hours. The polymer was precipitated into $CH_3OH$ and dried overnight under vacuum.

EXAMPLE 7

Slightly Cross-linked System

The reaction of Example 6 was repeated using the following quantities: MDI, 12.0 g; 2,4-D, 8.84 g; polyvinyl alcohol (99% hydrolyzed, high molecular weight) 10.0 g. A gel-like material formed five minutes after addition of polyvinyl alcohol to the reaction solution. The gel was converted to a microporous light yellow solid by precipitation in a Waring Blender.

EXAMPLE 8

5.04 g (0.03 moles) of hexamethylene diisocyanate was dissolved in 100 ml of dimethyl acetamide and added to 6.43 g (0.03 moles) of metribuzin in 100 ml of the same solvent. The mixture was heated to 100° C. and allowed to react for two hours. 6.0 g of polyvinyl alcohol (99% hydrolyzed, high molecular weight) was dissolved in 150 ml of hot dimethyl acetamide and added to the above solution at 110° C. After one hour at 110° C. the polymeric controlled release product was isolated by precipitating using methanol as the nonsolvent. A light-yellow product was obtained after drying overnight in a vacuum oven.

EXAMPLE 9

The above conditions were repeated using tolylene diisocyanate instead of HMDI to yield a light tan polymer.

Polymers from the above examples contain 20–30% pesticide by weight based on the final weight after drying. By proper adjustment of reactants, polymers can be prepared containing up to 60% or so of pesticide by weight. If desired, additives such as U.V. stabilizers, fillers and the like can be added to obtain polymer systems with a wide range of physical properties tailored to specific needs. Such tailoring, of course, is not possible when natural polymeric substances such as lignin are employed.

In order to evaluate the controlled or sustained release of the pesticide from the polymer systems, the following tests were performed.

1. Samples from the above described experiments were tested for release in distilled $H_2O$ over a period of weeks;
2. Aliquots were removed periodically and tested by:
    a. u.v. ($H_2O$ solution directly);
    b. gas chromatography on extracted portions;
3. Samples were carefully weighed prior to water immersion. Weighed after test; and
4. Soil tests were conducted.

The results of the tests indicated that the active pesticide in each instance was released on a controlled and sustained manner over an extended period of time.

Tests also were performed which demonstrate that the chemically bonded compositions of the present invention provide a more controlled and sustained release of the pesticide than is obtained with physical mixtures of the ingredients or by use of the pesticide alone. The results of some of those tests are summarized below and are reported in detail in my article entitled "Synthesis, Characterization and Release Mechanisms of Polymers Containing Pendant Herbicides", ACS Symposium Series, No. 53 on Controlled Release Pesticides, Copyright 1977.

In the tests, metribuzin was chosen as the model pesticide because of its amine functionality, its high activity at relatively low concentrations, its selectivity, its lack of persistence in the environment, and its high mobility. Polyvinyl alcohol was selected as the polymer because it is biodegradable and it is readily available commercially.

A brief description of the tests that were performed follows:

Five polymers containing pendant metribuzin were chosen for study. Three were essentially linear polymers prepared from 99% hydrolyzed polyvinyl alcohol, the other two were highly cross-linked microporous solids. The latter systems require both hydrolysis of the urea bond and diffusion from a water swollen, cross-linked matrix for metribuzin release.

Rates of Release of Metribuzin. The polymers with pendant metribuzin (0.100 g) were placed in an Erlenmeyer flask. 500 ml of distilled water was added. At designated intervals, samples were taken to determine the concentration of released metribuzin.

Ultraviolet Spectroscopic Method. A cary 1756 Spectrophotometer was used to determine released metribuzin levels in water. A standard plot of absorbance vs. concentration was obtained using least squares analysis. 3 ml samples were taken at designated intervals and placed in standard quartz cells. The absorbance at 293.5 nm was monitored in two types of tests. The first measured total concentration of released metribuzin over a time period. The second test was conducted as follows: (a) 0.100 g samples were placed in 500 ml of distilled water for a predetermined time; (b) the samples were filtered, dried and again placed in a second Erlenmeyer flask containing 500 ml of distilled water; (c) concentrations were measured directly from the filtrate.

Gas Chromatographic Method. 2 ul of aqueous solution were removed and extracted with 5.0 ml of benzene. 1 ul of the benzene phase was then injected into the gas chromatograph (Micro-Tek 220 with electron capture detector).

The different pesticide polymers released different levels of the pesticide at a controlled and sustained rate demonstrating that the compositions of the present invention can be tailored to provide desired rates and levels of release. Plots of solution concentration vs. time indicated that the linear polymers released herbicide much more rapidly than the cross-linked systems. The linear polymers were characterized by a rapid initial release in the first few hours followed by a more gradual rate lasting several days. The cross-linked systems had much lower release rates with little initial release. This could be predicted by the time required for swelling of the hydrophilic polymer so that hydrolysis and diffusion could occur. After swelling, slight concentration increases were noted. The u.v. spectroscopic data and the gas chromatographic data were internally consistent.

Soil Mobility Studies. In the study, thin-layer plates were prepared by spreading a soil slurry onto 20×20 cm glass plates to a thickness of 1.0 mm. Plates were divided into three equal sections by scribing the soil layer. Metribuzin was applied to one plate by streaking 500λ of a 100 g/ml solution onto each section of the plate 2 cm from the bottom. Polymer systems of the present invention containing pendant metribuzin were embedded in the soil layer on other plates which were also divided into three sections. The plates were eluted with 10 cm with water, air dried, and 1-cm zones were removed from one of the three sections of each plate. The plates were returned to the chamber and again eluted with 10 cm of water, and the second zone was removed in 1cm sections. This procedure was repeated with the third section of soil. The soil removed in this manner was extracted with 5 ml of hexane: acetone (3:1) by shaking. The extract was analyzed by gas chromatograph. The results of the tests demonstrated the sustained release capabilities of the pesticide-polymer systems.

Residual phytotoxicity tests were performed to illustrate the release of the pesticide, Metribuzin, from the polymer-pesticide systems. The polymer systems containing pendant Metribuzin were added to the surface of a Bosket sand loam soil contained in 4" plastic pots in a controlled-environment chamber. The application rates were 0, 0.1, 0.2, and 0.3 g of each formulation. A commercial formulation of metribuzin was applied to other pots at 0.5 and 1.0 ppmw, (concentrations known to be weed inhibiting) and thoroughly mixed into the soil. The soils were bioassayed over a period of 112 days with a mixture of weeds which are normally susceptible to the herbicide; after growing two weeks, the weeds were harvested and first weights recorded.

Soil thin-layer chromatographic techniques showed metribuzin moved as a normal chromatogram peak with each successive elution moving the peak nearer the 10-cm zone. The chromatograms from two of the linear polymer systems showed "streaking" continously along the plate indicating a sustained release mechanism. The cross-linked formulations did not release enough metribuzin for a measurable rate in these studies.

Residual phytotoxicity of the four polymeric systems was measured. The non-polymerically bound metribuzin at 1.0 ppmw had dissipated to a level which was essentially non-toxic after 78 days. Likewise, phytotoxicity from one of the pesticide-polymer systems had diminished to a large extent by this time. A relatively low level of phytotoxicity was observed for a cross-linked formulation initially; however, this same level was maintained for over 78 days, then rapidly decreased.

The highest level of phytotoxicity was observed with the linear polymers. These materials were still showing phytotoxicity at the last test date of 112 days.

Although in the above tests the comparisons were made between metribuzin and metribuzin linked by an isocyanate to polyvinyl alcohol the results would have been the same if a physical mixture of metribuzin and polyvinyl alcohol had been employed. In a physical mixture of metribuzin and polyvinyl alcohol, the metribuzin behaves in the same manner as if it alone were present.

The results of additional testing are described in detail in my article entitled "Biological Evaluation of Polymeric Controlled Activity Herbicides Systems Containing Pendant Metribuzin" from the Proceedings of 1978-Symposium on Controlled Release of Bioactive Material (August, 1978).

The pesticide-polymers of the present invention can be tailored to provide a variety of products with different degrees of substitution and/or cross-linking to provide different rates of release of effective amounts of a specific pesticide. The resulting pesticide-polymers are novel, useful products which can be used in the same manner as conventional pesticides. For example, they can be powdered, granulated and sprayed, dusted or otherwise applied to the crops or soil to: (1) reduce environmental pollution by reducing pesticide mobility, (2) reduce the number of applications required during the growing season, and/or (3) result in enhanced agricultural production.

It will be readily apparent to those skilled in the art that a number of modifications and changes can be made without departing from the spirit and scope of the present invention. Similar results to those reported can be achieved with pesticide-polymers including other known pesticides, including those previously named (e.g. 2,4-D). Therefore, it is not intended that the invention be limited by the illustrative examples but only by the claims which follow.

I claim:

1. A pesticide polymer, which has a macromolecular backbone with pendant pesticidal groups chemically linked thereto by linkages which are broken under environmental conditions of use to controllably release an effective amount of active pesticide, is prepared by reacting a pesticide having a replaceable hydrogen with a multifunctional organic isocyanate to form a pesticide-isocyanate adduct and then reacting the adduct with a polymer having pendant groups containing a replaceable hydrogen, to form linkages which are cleaved under enviromental conditions of use to controllably release an effective amount of pesticide.

2. The pesticide polymer of claim 1 in which the replaceable hydrogen of the polymer is derived from a pendant hydroxyl group.

3. The pesticide polymer of claim 1 in which the replaceable hydrogen of the pesticide is derived from a group selected from hydroxyl, sulfyhydryl, amino, imino, carboxyl, amido, sulfonamido, sulfonimido, phosphoramido, phosphorimido, thiophosphoramido, and thiophosphorimido.

4. A pesticide-polymer of claim 1 in which the pesticide is 4-amino-6-tert-butyl-3-(methylthio)-as-triazin-5(4H)-one.

5. A pesticide-polymer of claim 1 in which the polymer is polyvinyl alcohol.

6. The method of preparing a pesticide-polymer for the controlled release of pesticide under field of use conditions which comprises reacting a pesticide having a replaceable hydrogen with a multifunctional organic isocyanate to form a pesticide-isocyanate adduct and then reacting the adduct with a polymer having pendant groups containing a replaceable hydrogen to form a pesticide-polymer in which the pesticide is linked chemically to the pendant groups by linkages which are cleaved under environmental conditions of use to controllably release an effective amount of the active pesticide.

7. The method of claim 6 in which the replaceable hydrogen of the polymer is derived from hydroxyl groups.

8. The method of claim 6 in which the reaction is carried out in a mutual solvent for the polymer and the pesticide-isocyanate adduct.

9. The method of claim 1 in which the pesticide is 4-amino-6-tert-butyl-3-(methylthio)-as-triazin-5(4H) one.

10. The method of claim 1 in which the polymer is polyvinyl alcohol.

* * * * *